(12) United States Patent
Karasz et al.

(10) Patent No.: US 9,795,239 B1
(45) Date of Patent: Oct. 24, 2017

(54) DRAPE-CLAMPING REFERENCE ARRAY CONNECTOR

(71) Applicant: Brainlab AG, Munich (DE)

(72) Inventors: Stephan Karasz, Feldkirchen (DE); Rupert Heigl, Markt Schwaben (DE); Norman Plassky, Erfurt (DE); Brian Vasey, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/621,765

(22) Filed: Jun. 13, 2017

Related U.S. Application Data

(63) Continuation of application No. 13/983,795, filed as application No. PCT/EP2011/052216 on Feb. 15, 2011, now Pat. No. 9,706,868.

(51) Int. Cl.
| | |
|---|---|
| *A47H 13/01* | (2006.01) |
| *A61B 90/50* | (2016.01) |
| *A61B 50/28* | (2016.01) |
| *A61B 46/00* | (2016.01) |
| *A61B 46/20* | (2016.01) |
| *A61B 90/57* | (2016.01) |
| *A61B 46/10* | (2016.01) |

(52) U.S. Cl.
CPC .............. *A47H 13/01* (2013.01); *A61B 46/00* (2016.02); *A61B 46/20* (2016.02); *A61B 50/28* (2016.02); *A61B 90/50* (2016.02); *A61B 46/10* (2016.02); *A61B 2090/571* (2016.02)

(58) Field of Classification Search
CPC ......... A61B 46/00; A61B 46/10; A61B 46/20; A61B 50/28; A61B 90/50; A61B 2090/571; A47H 13/01

USPC ............................ 16/93 D, 94 D, 95 D, 96 D
See application file for complete search history.

(56) References Cited

U.S. PATENT DOCUMENTS

| 3,137,027 A | 6/1964 | Birkle |
| 3,205,547 A | 9/1965 | Riekse |
| (Continued) | | |

FOREIGN PATENT DOCUMENTS

| AT | 272564 | 8/2004 |
| CA | 2655861 | 6/2007 |
| (Continued) | | |

OTHER PUBLICATIONS

Written Opinion of the International Searching Authority for PCT/EP2011/052216, pp. 1-6.

(Continued)

*Primary Examiner* — Eret McNichols
(74) *Attorney, Agent, or Firm* — Tucker Ellis LLP

(57) ABSTRACT

A connector for attaching a reference array in a fixed positional relationship with respect to a patient to be covered by a sterile drape in an attachment area, includes a support to be situated below the drape and a clamping element which is to be situated above the drape and can directly or indirectly hold the reference array or a reference array adaptor, wherein the clamping element clamps the support, with the drape caught between the two, by at least two distinct clamps which clamp the support from at least partly opposing directions in such a way that the positional shift in the clamping element as a result of clamping the drape at the clamping position is compensated for, such that its overall positional shift is substantially zero. A method attaching a reference array in a fixed positional relationship relative to a patient above a sterile drape is also provided.

12 Claims, 9 Drawing Sheets

(56) References Cited

U.S. PATENT DOCUMENTS

| | | |
|---|---|---|
| 3,296,668 A | 1/1967 | Aiken |
| 3,924,303 A | 12/1975 | Elliott |
| 4,288,733 A | 9/1981 | Bilanceri et al. |
| 4,522,196 A | 6/1985 | Cunningham et al. |
| 4,759,087 A | 7/1988 | Zeilinger |
| 5,311,358 A | 5/1994 | Pederson et al. |
| 5,419,343 A | 5/1995 | Taylor |
| 5,467,223 A | 11/1995 | Cleveland, Jr. et al. |
| 5,591,119 A | 1/1997 | Adair |
| 5,792,045 A | 8/1998 | Adair |
| 5,876,328 A | 3/1999 | Fox et al. |
| 5,979,450 A | 11/1999 | Baker et al. |
| 6,142,153 A | 11/2000 | Monroe |
| 6,202,801 B1 | 3/2001 | Muller et al. |
| 6,375,610 B2 | 4/2002 | Verschuur |
| 7,993,353 B2 | 8/2011 | Roβner et al. |
| 8,074,657 B2 | 12/2011 | Scott et al. |
| 8,206,406 B2 | 6/2012 | Orban, III |
| 8,578,571 B2 | 11/2013 | Schmidt et al. |
| 2003/0196668 A1 | 10/2003 | Harrison et al. |
| 2003/0217446 A1 | 11/2003 | Hamlin et al. |
| 2003/0225329 A1 | 12/2003 | Rossner et al. |
| 2005/0094269 A1 | 5/2005 | Moses et al. |
| 2005/0096536 A1 | 5/2005 | Peterson |
| 2006/0139753 A1 | 6/2006 | Moses et al. |
| 2010/0268249 A1 | 10/2010 | Stuart |
| 2011/0219534 A1 | 9/2011 | Hu et al. |
| 2014/0026359 A1 | 1/2014 | Borgerding et al. |
| 2014/0261456 A1 | 9/2014 | Malackowski et al. |
| 2014/0318551 A1 | 10/2014 | Daly |
| 2015/0000676 A1 | 1/2015 | Colona |
| 2015/0257570 A1 | 9/2015 | Ferk |
| 2015/0282735 A1 | 10/2015 | Rossner |
| 2015/0297315 A1 | 10/2015 | Fowler et al. |
| 2015/0351848 A1 | 12/2015 | Ghosh |
| 2015/0351857 A1 | 12/2015 | Poorten et al. |
| 2015/0374442 A1 | 12/2015 | Corenman et al. |

FOREIGN PATENT DOCUMENTS

| | | |
|---|---|---|
| CH | 425114 | 11/1966 |
| CH | 454378 A | 4/1968 |
| DE | 876755 C | 5/1953 |
| DE | 1135631 | 8/1962 |
| DE | 1230976 B | 12/1966 |
| DE | 1919055 A1 | 10/1970 |
| EP | 0955014 A1 | 11/1999 |
| EP | 0984794 A | 3/2000 |
| FR | 1601503 A | 10/1970 |
| GB | 311960 A | 5/1929 |
| JP | 2006061272 | 3/2006 |
| WO | 2005044127 A1 | 5/2005 |
| WO | 2010054836 A2 | 5/2010 |

OTHER PUBLICATIONS

International Preliminary Report on Patentability for PCT/EP2011/052216, pp. 1-7.

European Patent Office, office action dated Aug. 16, 2017, for corresponding EP11706197.8 application consisting of 6 pages.

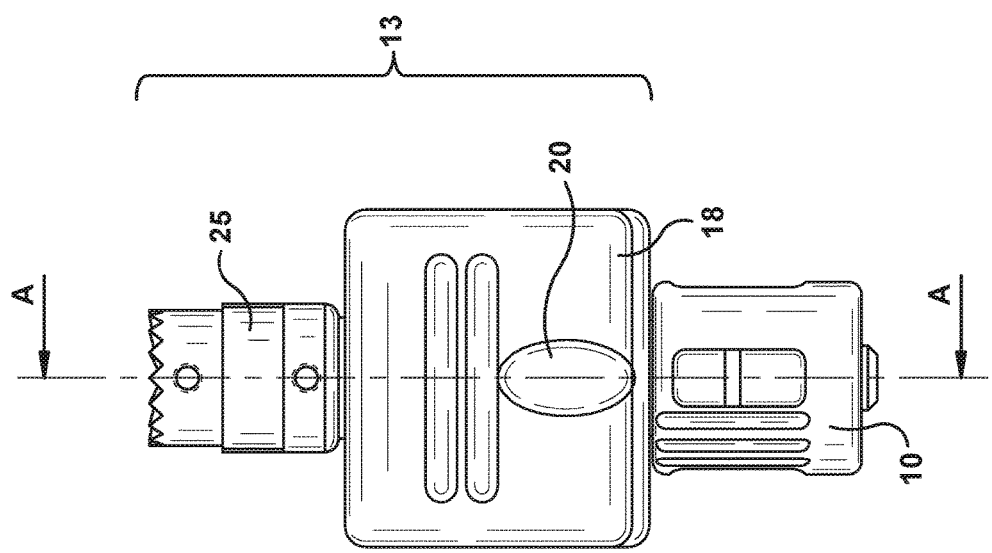
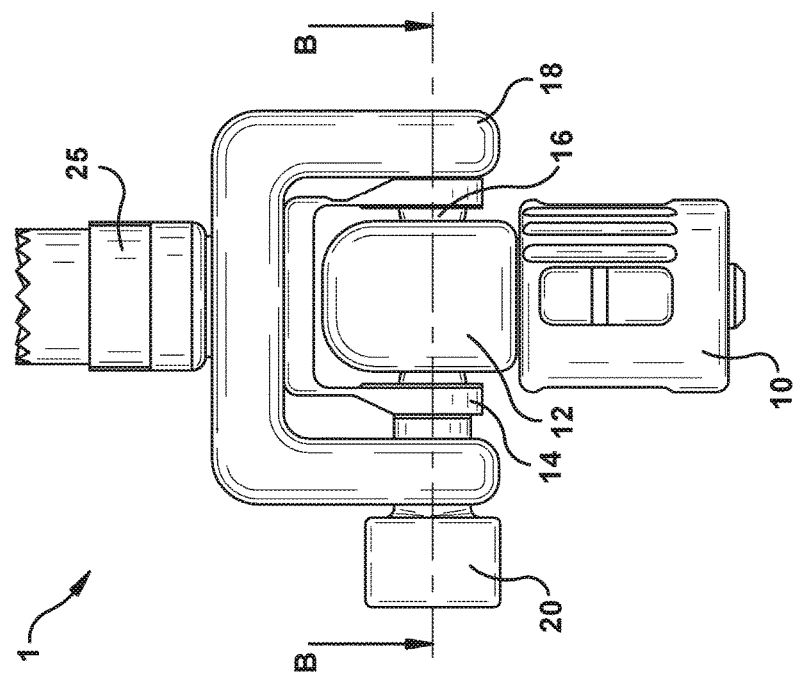

DRAPE-CLAMPING REFERENCE ARRAY CONNECTOR

CROSS REFERENCE TO RELATED APPLICATIONS

This application is a continuation of U.S. application Ser. No. 13/983,795, filed Aug. 6, 2013 which is the U.S. National Stage of International Application No.: PCT/EP2011/052216 filed Feb. 15, 2011, the entire contents of each of which are incorporated herein by reference.

The present invention relates to a connector for attaching a reference array in a fixed positional relationship with respect to a patient. Such reference arrays serve as means for positionally tracking a patient in an image-guided surgery system or surgical navigation system. By detecting the position of the reference array (by means of a detector such as a camera system), the position of the patient can be registered and tracked during medical imaging and/or treatment.

One problem which often arises when attaching reference arrays is that of preserving sterility while keeping the reference array visible to its detector, for example the camera system. While the patient will be covered by sterile drapes in order to ensure the sterility of the vicinity of the treatment location, any reference array should be arranged outside the sterile drape, but should be located relatively close to the treatment location in order to obtain a high level of accuracy. Because the patient attachment for the reference array is below the drape and the reference array itself needs to be above the drape, a drape always comes between the two. In the prior art, the drape is therefore cut so that the connector for the reference array can protrude through the cut in order to mount the reference array.

It is evident that cutting the drape compromises its sterility, even if efforts are made to re-seal the drape as tightly as possible.

Merely clamping the uncut drape between the connector interface and the interface of the reference array does not work at all with typical connectors which have a threaded interface. Other connectors, which could in principle clamp the drape between the connector interface and the array interface, would still not be feasible because the presence of the drape and any wrinkles which may be formed in it will alter the positional relationship between the array and the connector as compared to a scenario in which they are fixed without the drape between them. However, first registration procedures using a reference array are carried out without a drape over the patient, while navigation is performed after the patient has been sterilely draped, hence the aforementioned positional shift would render the registration results obsolete or the navigation results inaccurate.

It is an object of the present invention to provide a way of retaining the accuracy and validity of a registration result obtained using a reference array which is to be attached to a patient in a draped and an undraped state. It is another object of the present invention to provide a drape-clamping reference array connector which ensures that a reference array is reproducibly attached, whether the patient is draped or not.

These objects are achieved by a connector in accordance with claim 1 for attaching a reference array in a fixed positional relationship with respect to a patient. Using the same inventive concept, the present invention also provides a connector arrangement in accordance with claim 12 comprising such a connector, and a method in accordance with claim 13 for attaching a reference array in a fixed positional relationship with respect to a patient. The sub-claims define advantageous embodiments of the present invention.

The connector of the present invention is to be used in cases in which the patient is to be covered by a sterile drape in the attachment area. The connector comprises a support which is to be situated below the drape and a clamping element which is to be situated above the drape and can directly or indirectly hold the reference array or a reference array adaptor, wherein the clamping element clamps the support, with the drape caught between the two, by means of at least two distinct clamps which clamp the support from at least partly opposing directions in such a way that the positional shift in the clamping element as a result of clamping the drape at the clamping position is compensated for, such that its overall positional shift is substantially zero.

In other words, the present invention has recognized that clamping a drape will slightly shift the clamping object itself, has found a way to use precisely this positional shift at suitable locations in order to bring the array to be attached back to the position used during registration. Thus, features which in principle represent a disadvantage (i.e. the positional shift) have been purposefully utilized and so turned into advantageous features.

Using the connector in accordance with the present invention, an attached array will be at the same location, whether a drape is present or not. Since the drape does not then have to be cut, this arrangement necessarily retains 100% sterility, while allowing the registration results to remain accurate at all times and thus keeping the navigational accuracy at its highest level. The connector of the present invention also allows the reference array to be reproducibly attached, detached and re-attached as often as is necessary during workflows including registration, navigation and intra-operative imaging.

In one embodiment of the connector of the present invention, the clamps form a non-continuous clamping area, in particular distinct clamping contacts or distinct clamping contact areas. This aids in providing a highly reproducible clamping situation, as it avoids doubled-over layers or wrinkled drape portions be clamped over a larger area, which could lead to unpredictable shifts in position. Another advantage is provided if the clamps and the support are provided with positioning elements and counter elements at the contact points or contact areas, in order to facilitate setting or installing the clamping element at the correct location on the support.

Using the principle of the present invention, there are various ways of arranging the clamps of the clamping element with respect to the support. Some of these arrangements, which can also be combined, are detailed below:
  the clamps clamp the surface of the support from directions which are orientated towards a symmetrical feature, in particular a plane or an axis of symmetry, of the support and/or its surface;
  the clamps are arranged on different sides of the support and clamp it from directly opposing or parallel directions;
  the clamps, in particular three or more clamps, are distributed, in particular uniformly, along parallel flat surfaces of the support and clamp it in parallel and/or anti-parallel and/or coincident and/or opposing directions;
  the clamps, in particular three or more clamps, are distributed, in particular uniformly, along a curved surface or angled flat surfaces of the support and clamp it from directions which intersect substantially at one point and in particular have an intersecting point which is arranged substantially on a plane or an axis of symmetry of the support;

the clamps are arranged such that their clamping direction lies at a right angle or parallel to the direction of a reference array holder which extends from the clamping element.

It is to be noted that the arrangement of the clamps can be chosen from any range of possible arrangements, as long as the overall shift resulting from clamping the drape amounts to a substantially zero-value positional shift in the clamping element. In this respect, it is also possible to additionally use a plurality of clamps which directly contact the support, as long as these direct contacts do not influence the overall compensation for the drape thickness or alternatively as long as said direct contacts are compensated for by other direct and/or drape-clamping contacts.

In one advantageous embodiment, clearances between the clamping element and the surface of the support for freely accommodating drape material are provided in between the contact points/areas of the clamps. The clearances can of course be formed by the clamping element alone, the clamping element and the support, or the support alone. The drape can rest freely in such clearances and will therefore not influence the position of the clamping element. Any wrinkles or double-layering within these clearance areas will also not influence the registration results or the navigational accuracy.

The clamping element can form a bracket, in particular a flexible bracket, in particular a forked bracket. It can comprise clamping arms which are or can be flexibly biased towards their clamping positions, wherein the arms are in particular rendered flexible by thinner arm portions which are spaced away from their clamping ends. In such an embodiment, the clamping arms or their ends are or can be biased in the direction of the support by at least one biasing element, in particular a screw which is anchored on a rigid holder which accommodates or encompasses the clamping element. In order to provide balanced forces on the support, this rigid holder can be slidably mounted on the clamping element.

In accordance with one embodiment of the present invention, the clamps and the support can be slidably engaged at the clamping positions, such that their clamping force direction is substantially constant and does not depend on any movements or bending by the clamping element. The clamps and the support can also have corresponding, in particular snugly fitting, surface forms at the clamping positions, such as extensions and receptacles, in particular convex and concave parts or hemispheres. Such surface forms enable the clamping element to be reproducibly attached to the support.

In accordance with another embodiment of the connector according to the present invention, the clamping element comprises clamping arms which can be slidably moved towards their clamping positions, in particular slidably arranged on a linear guide, such that their sliding movement is a movement along a linear axis. Such an arrangement allows the clamping arms to be bent as little as possible during or before the attachment process, such that even very small positional shifts resulting from the biased and curved clamping arms can be avoided.

It can sometimes be necessary to place a reference array at a higher position, for example in order to provide better visibility. On the other hand, it can be necessary to provide a sterile adaptor and maintain its sterility while attaching another connector above the sterile field, for example in order to provide a tracking reference for registration before or after an intra-operative imaging step. In order to adapt the present invention as hitherto described to these requirements, a connector arrangement is provided which comprises a first connector such as has been described above in several embodiments. The connector arrangement also comprises a second clamping unit which is clamped to the first clamping unit of the first connector. In this respect, the term "clamping unit" is used to denote the assembly consisting of the elements of the connector which are clamped onto the support, namely the clamping element and the elements connected to it—in other words, all the elements of the connector which remain above the drape, apart from the reference array itself. In one embodiment, the connector arrangement comprises a second, intermediate support which is attached to the upper portion of the first clamping unit, i.e. above the clamping element and on top of the first clamping unit, such that a second clamping unit can be clamped onto said intermediate support.

In general terms, the method of the present invention provides the same advantages as have been described above with reference to the connector. The method serves to attach a reference array in a fixed positional relationship with respect to a patient and comprises the following steps:

covering the patient with a sterile drape and thereby covering a connector support which is directly or indirectly attached to the patient or a patient holding device;

fastening a clamping element above the drape, wherein the clamping element directly or indirectly holds the reference array or a reference array adaptor, and wherein the clamping element clamps the support, with the drape caught between the two, by means of at least two distinct clamps which clamp the support from at least partly opposing directions in such a way that the positional shift in the clamping element as a result of clamping the drape at the clamping position is compensated for, such that its overall positional shift is substantially zero.

The connector as described above in various embodiments can of course be used in the method of the present invention.

In the following, the invention will be described in more detail by referring to particular embodiments and to the attached drawings. It is to be noted that each of the features of the present invention as referred to herein can be implemented separately or in any expedient combination. In the drawings:

FIGS. 1 to 5 show an embodiment of a connector according to the present invention, in various views and sections;

Figure 4:
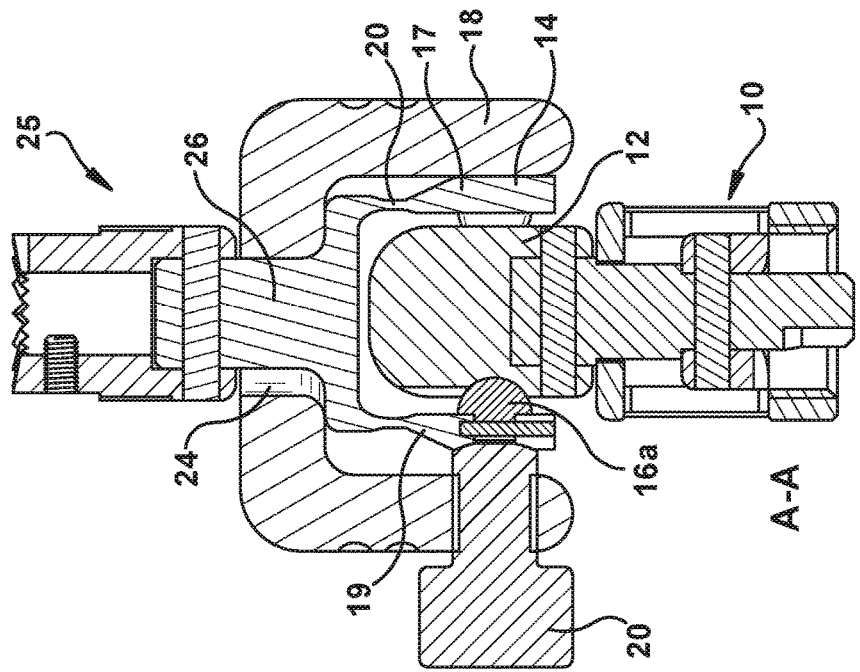
Figure 3:
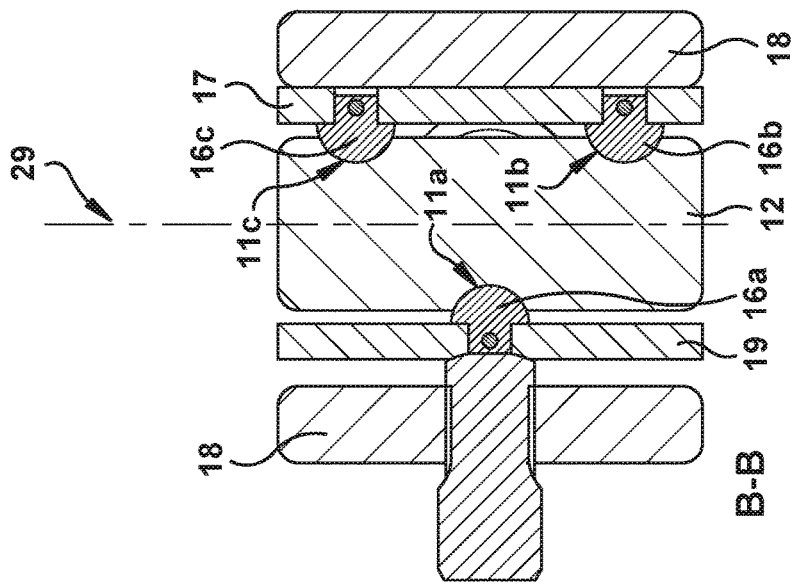
Figure 5:
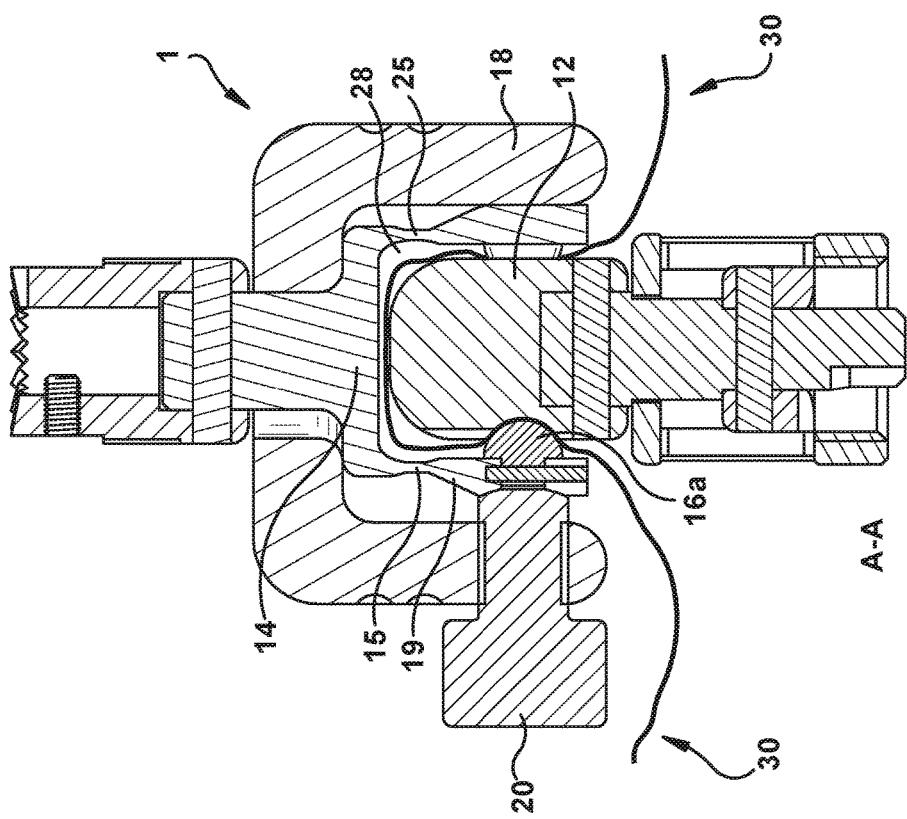

One embodiment of a connector according to the present invention is shown in FIGS. 1 to 5. The connector as a whole has been given the reference numeral 1. It consists of a lower part 10 which is to be fixed for example to any device which is immovably attached to a patient, and the support 12 which acts as a clamping block. The clamping unit, which as a whole has been given the reference numeral 13 in FIG. 2, is positioned above the support or clamping block 12 and comprises a clamping element or fork 14 which comprises hemispherical clamps 16a, 16b and 16c on its clamping arms 17, 19. One clamp 16a is arranged in the middle portion of one clamping arm, namely the clamping arm 19 as indicated in FIGS. 3 to 5. The other clamping arm which opposes the clamping arm 19 has been given the reference numeral 17, and in FIG. 3 (which corresponds to the section A-A from FIG. 2), it can be seen that two hemispheres 16b and 16c are positioned on the inner side of the clamping arm 17. The clamping unit 13 also comprises a rigid holder or slider 18 which has an opening 24 in its centre part such that it can be slidably arranged over the neck 26 of the fork 14. The left arm of the rigid holder 18 comprises a screw 20 which, as can be seen in FIGS. 3 to 5, can be screwed in, such that its right-hand front face presses the clamping arm 19 towards the support 12 and the hemispheres 16a, 16b and 16c are thus sunk into respective hemispherical recesses which have been given the reference numbers 11a, 11b and 11c in FIG. 3. Because the rigid holder 18 is slidably guided on the neck 26 of the clamping element 14, the force of the screw 20 is balanced and acts upon the support 12 via the hemispheres 16b and 16c.

A reference array holder 25 is mounted to the upper part of the neck 26 of the clamping element 14. A reference array can be fixedly attached to the holder 25.

In general terms, the function of the connector 1 can be described as follows.

The lower part 10 is fixed to the patient, most probably by a device which is immovably fixed to the patient or the part of the patient which is to be treated. Thus, the clamping block 12 which is fixed to the lower part 10 will protrude in the vicinity of the treatment region.

In order to provide a sterile operating field, a drape— shown as 30 in FIG. 5—is then placed over the patient and the clamping block 12, and the clamping unit 13 (FIG. 2) can be clamped over the drape-covered clamping block 12, as explained below.

With the screw 20 in a retracted position, i.e. moved to the left-hand side in FIGS. 1, 3, 4 and 5, the clamping unit 13 can be assembled in such a way that the holder 18 is positioned with its opening 24 on the neck 26, and the legs of the holder 18 extend parallel to and on the outside of the clamping arms 17, 19 of the clamping element or fork 14. The reference array holder 25 can then be installed on top of the neck 26. In this state, the clamping arms 17, 19 of the fork 14 extend parallel and downwards, and because the screw is retracted to the left, the clamping arms 17, 19 can be bent outwards due to the flexibility afforded by the recessed or thinner areas 15 which can be seen in FIGS. 4 and 5. It is to be noted that such thinner portions 15 may not be needed if the material of the clamping element 14 is itself sufficiently flexible or resilient.

As shown in FIG. 5, a drape 30 is placed over the support 12 in the process of covering the patient. FIG. 5 shows the final state of fixation (as do FIGS. 1 to 4) which is achieved by pressing the entire clamping unit 13, with the screw 20 missing or in its far left position, down onto and over the rounded edges of the support or clamping block 12 from above. The pressure exerted bends the clamping arms 17, 19 outwards until the hemispheres 16, having glided along the draped surface of the support 12, enter their respective receptacles 11. The screw 20 can then be screwed inwards such that its front face engages with the outer surface of the clamping arm 19 and, when moved further to the right, presses the clamping arm 19 onto the support 12 (and the hemispheres 16 into their respective receptacles 11) in order to securely fix the clamping unit 13 to the support 12. In the example shown, and as can be seen in FIG. 3, the force is exerted on the support 12 at three locations 16a, 16b and 16c, but is equally balanced because the holder 18 can move freely with its opening 24 surrounding the neck 26.

What is even more important is that when clamping the drape and therefore the reference array holder 25, the clamping element 14 does not exhibit any difference in position as compared to when a drape is not present. Although the presence of the drape between the hemisphere 16a and the receptacle 11a moves the clamping element 14 to one side, for example to the left in FIG. 3, its presence on the opposite side of the support 12 moves the clamping arm 17 to the left by exactly the same distance. This is guaranteed among other things by the use of distinct clamping points, which enables wrinkles to be avoided. This is the case in the embodiment discussed here, although other forms of avoiding such wrinkles are also conceivable.

Overall, the positional shift acting on the clamping element 14, and therefore on the reference array mounted on it, is balanced due to the attachment method and the connector design detailed above. A physician's team can therefore be certain that a reference array which is attached in accordance with the present invention, for example in accordance with the embodiment of FIGS. 1 to 5, will remain at the same position in relation to the patient, irrespective of whether a drape is covering the patient and the support or not. The height of the reference array holder 25 is in no way influenced by the presence of the drape, because of the clearance 28 between the support 12 and the inner surface of the clamping element 14, which can accommodate even larger quantities of wrinkled drape.

A second drape and therefore a second connector may be needed in order to carry out intra-operative imaging. Although two drapes could in principle be clamped using one connector such as that shown in FIGS. 1 to 5, it may be necessary and/or desirable to keep the connector used first, in particular its clamping unit 13, sterile, for which purpose the present invention proposes the use of a connector arrangement as shown for example in FIGS. 6 and 7. This connector arrangement as a whole has been given the reference numeral 2 and consists substantially of two connectors, one mounted on the other. Specifically, the lower clamping unit 13 has been modified as compared to the clamping unit of FIGS. 1 to 5 by replacing the reference array holder 25 with a second support 22 which is fixedly mounted. A second clamping unit 23 has been placed on this support 22 and fixed as described above. The second clamping unit 23 comprises the reference array holder 34 at its upper end. Using this arrangement, a first drape can be placed between the support 12 and the clamping unit 13, and a second drape could be placed between the support 22 and the clamping unit 23 without shifting the overall position of the arrangement as a whole and in particular the reference array holder 34. FIG. 8 shows two drapes 30 and 32 clamped by a connector arrangement, in a sectional view.

Figure 7:
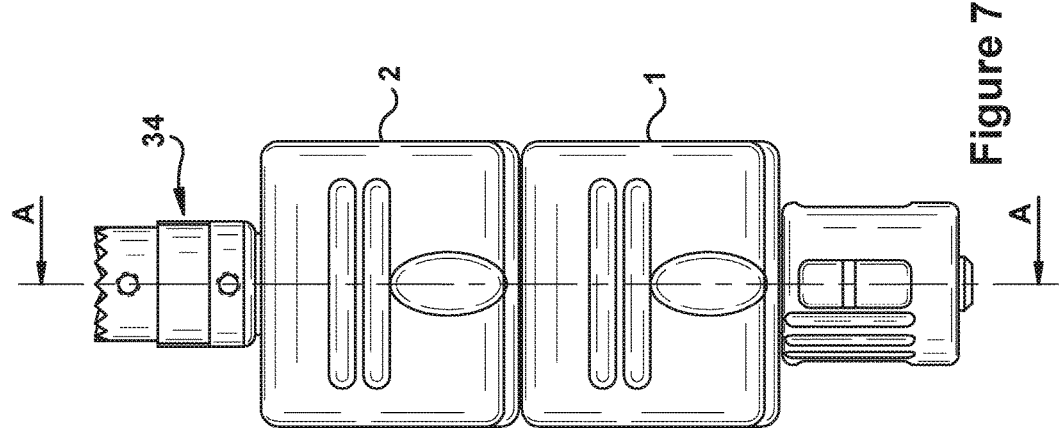
FIGS. 6 to 8 show a connector arrangement including two connectors according to the present invention.
Figure 6:
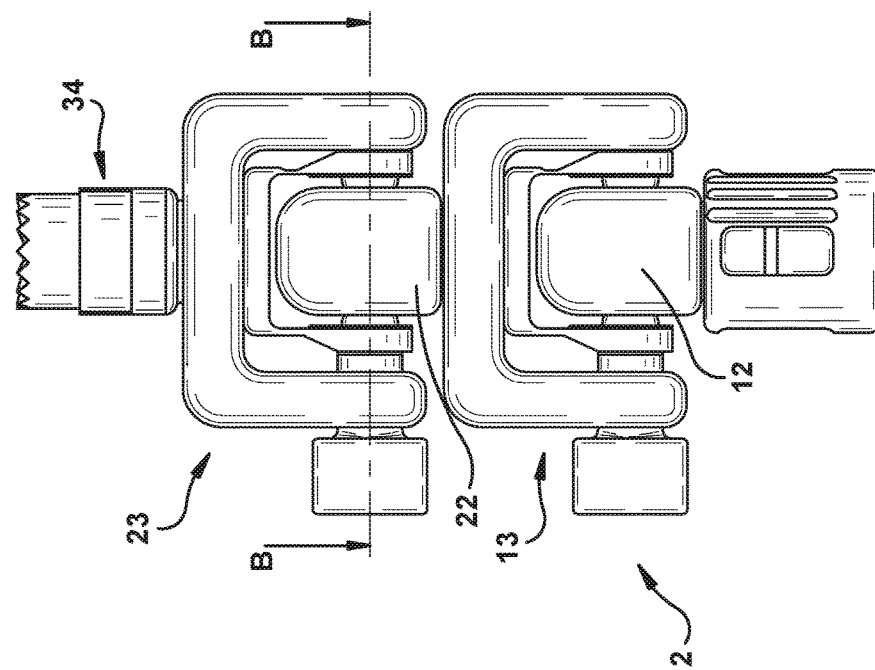
Figure 8:
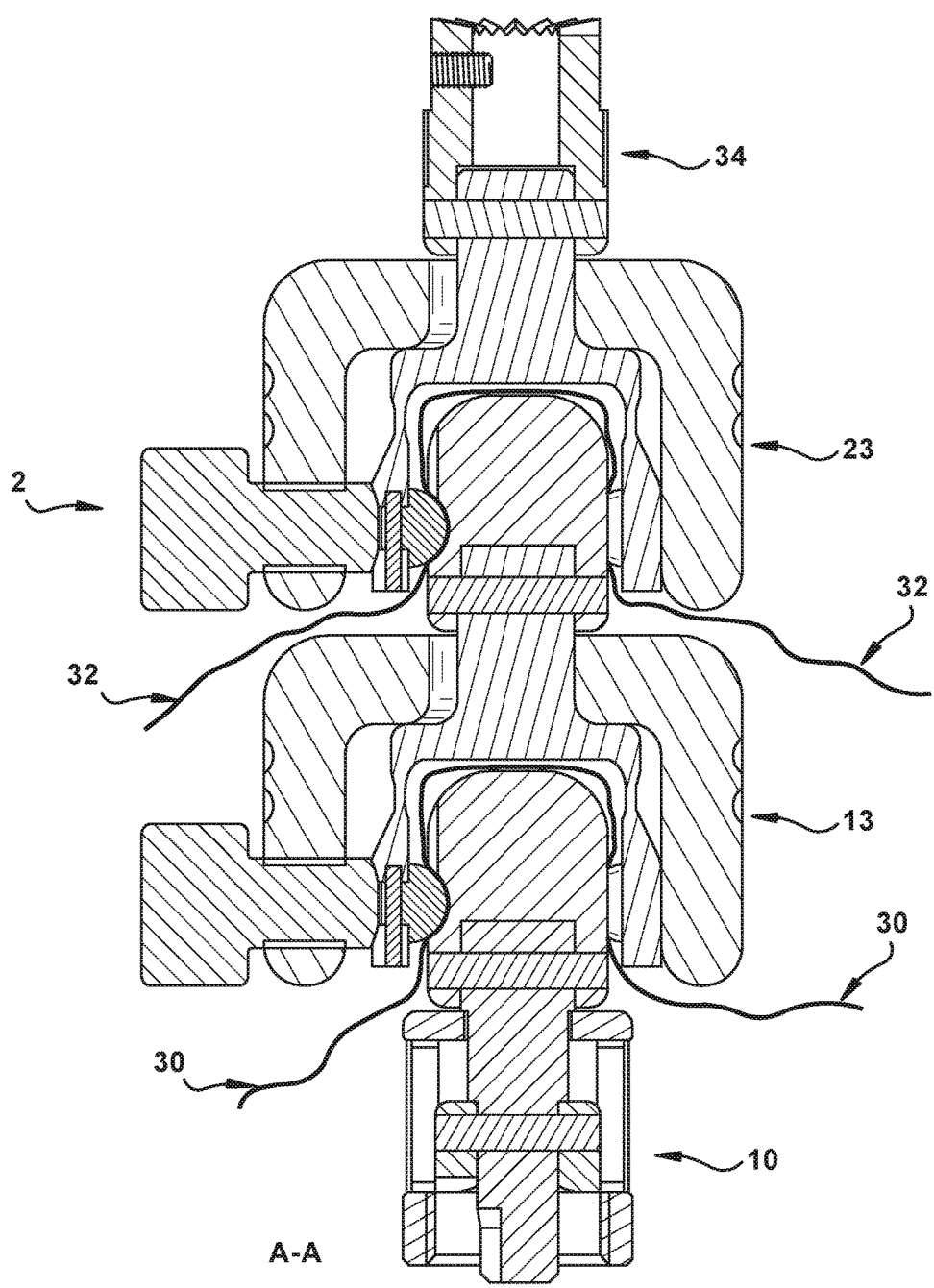

The arrangement of FIGS. 6 and 7 comprising two connectors has another advantage, namely that each of the clamping units 13 and 23 only needs to clamp one drape, thus avoiding any increased wrinkling effect which might be incurred when clamping two drapes at one location.

Figure 9:
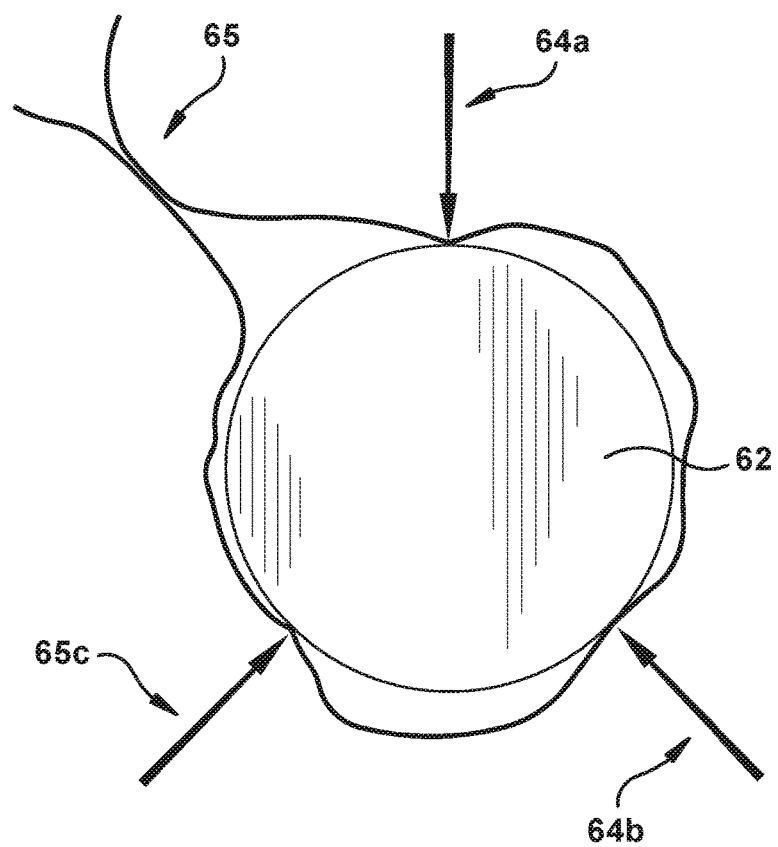
FIG. 9 shows an alternative way of clamping a support.

As mentioned above, a connector according to the present invention can be embodied in various ways. While the drape is clamped in parallel or anti-parallel directions orientated according to the longitudinal axis plane 29 (FIG. 3) in the embodiments of FIGS. 1 to 8, the clamps can also act in different directions, as shown for example in FIG. 9, in which a cylindrical support 62 is shown in a simplified front-face view. Similarly, three clamps (or more specifically their acting directions) 64a, 64b and 64c are shown which act in directions which are respectively shifted with respect to each other by 120 degrees. The present invention is again embodied if the cylindrical support 62 in such an arrangement is covered with a drape 65, since the outwardly orientated positional shifts in the clamps 64a, 64b and 64c caused by the thickness of the drape are balanced and have an overall value equal to zero. If the clamps 64a, 64b and 64c were mounted on a single clamping element, the overall position of the clamping element (in the plane of the drawing) would not be changed by the drape.

Figure 10:
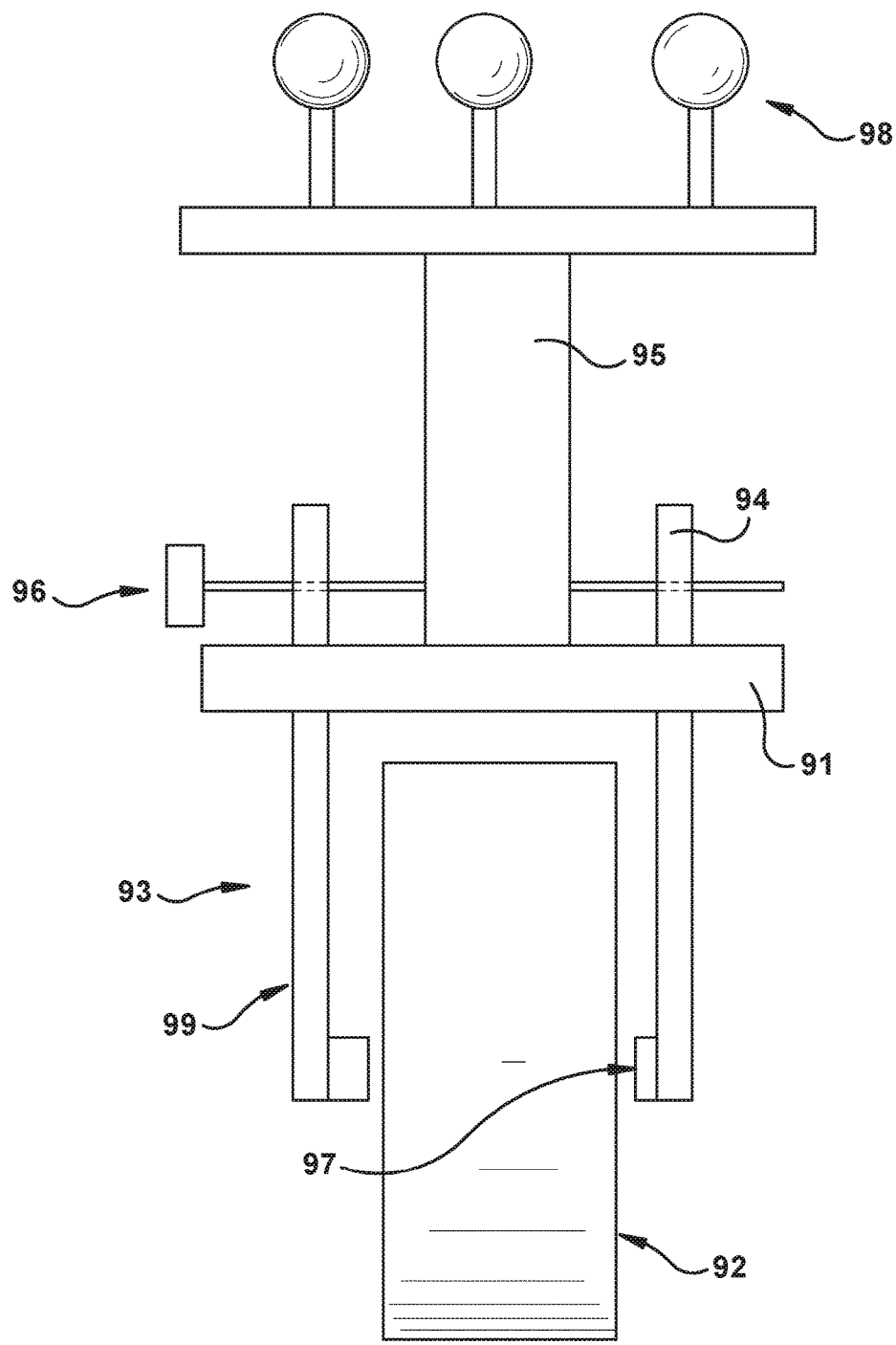
FIG. 10 shows a clamping unit comprising clamps which run on a linear guide.

FIG. 10 shows an embodiment of a clamping unit 93 in which the clamping force is not primarily generated by the resilience or flexibility of the clamping arms. The clamping arms 97, 99 of the clamping unit 93 are slidably mounted on a guide rail 91—in the embodiment of FIG. 10, the left arm can slide while the right arm is fixed. The reference array holder 95 holds the reference array 98 and is fixedly attached to the guide rail 91.

Turning the screw 96, which is axially fixed but rotationally movable in the upper part 94 of the right-hand clamping arm 97, moves the left-hand clamping arm 99 to the right, such that the support 92 is clamped between the two clamping arms 97, 99. If the clamping arms 97, 99 and the guide rail 91 are sufficiently rigid, the clamping force can be exerted without having to depend on any particular resilience or flexibility in the clamping arms 97, 99. Thus, even very small positional shifts which might result from the clamping element flexibly or resiliently bending can be avoided.

A workflow using a connector and/or connector arrangement in accordance with the present invention will now be described with reference to FIGS. 11 and 12. The connectors are shown in the workflow of FIGS. 11 and 12 in a simplified manner and have therefore been given new reference numerals, but they are designed in accordance with the present invention and can be connectors in accordance with the embodiments discussed above with reference to FIGS. 1 to 10.

The workflow includes the steps of imaging a patient, registering the patient and navigating with respect to the patient by means of a surgical tracking and navigation system. Intra-operative imaging forms one step of the workflow, in order for example to compensate for positional shifts in tissue during the treatment.

Figure 11:
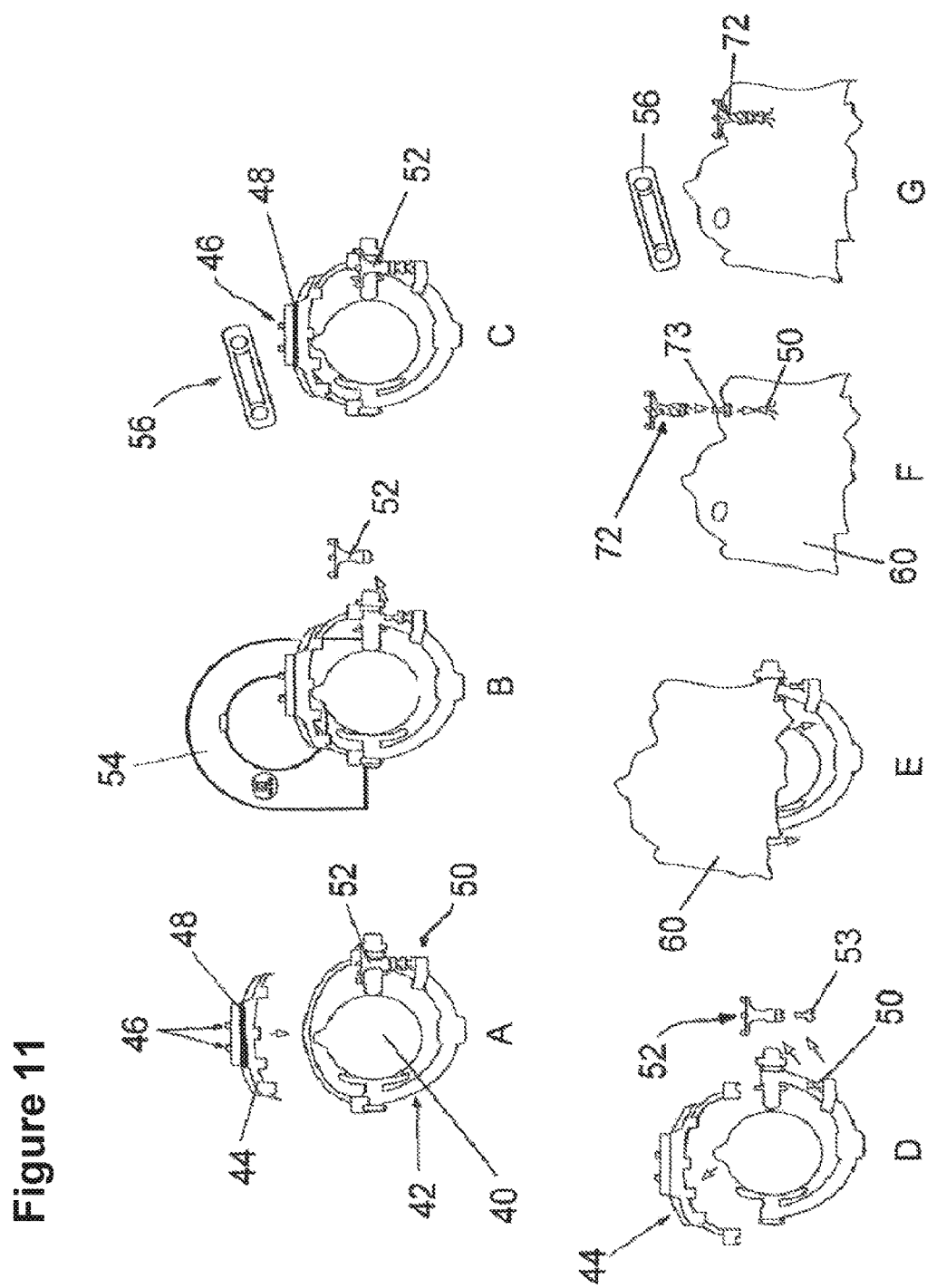
FIGS. 11 and 12 show a workflow including the steps of imaging a patient and placing a drape over the patient, as well as steps of registering and navigating by means of a reference array which is attached to the patient via a connector according to the present invention.
Figure 12:
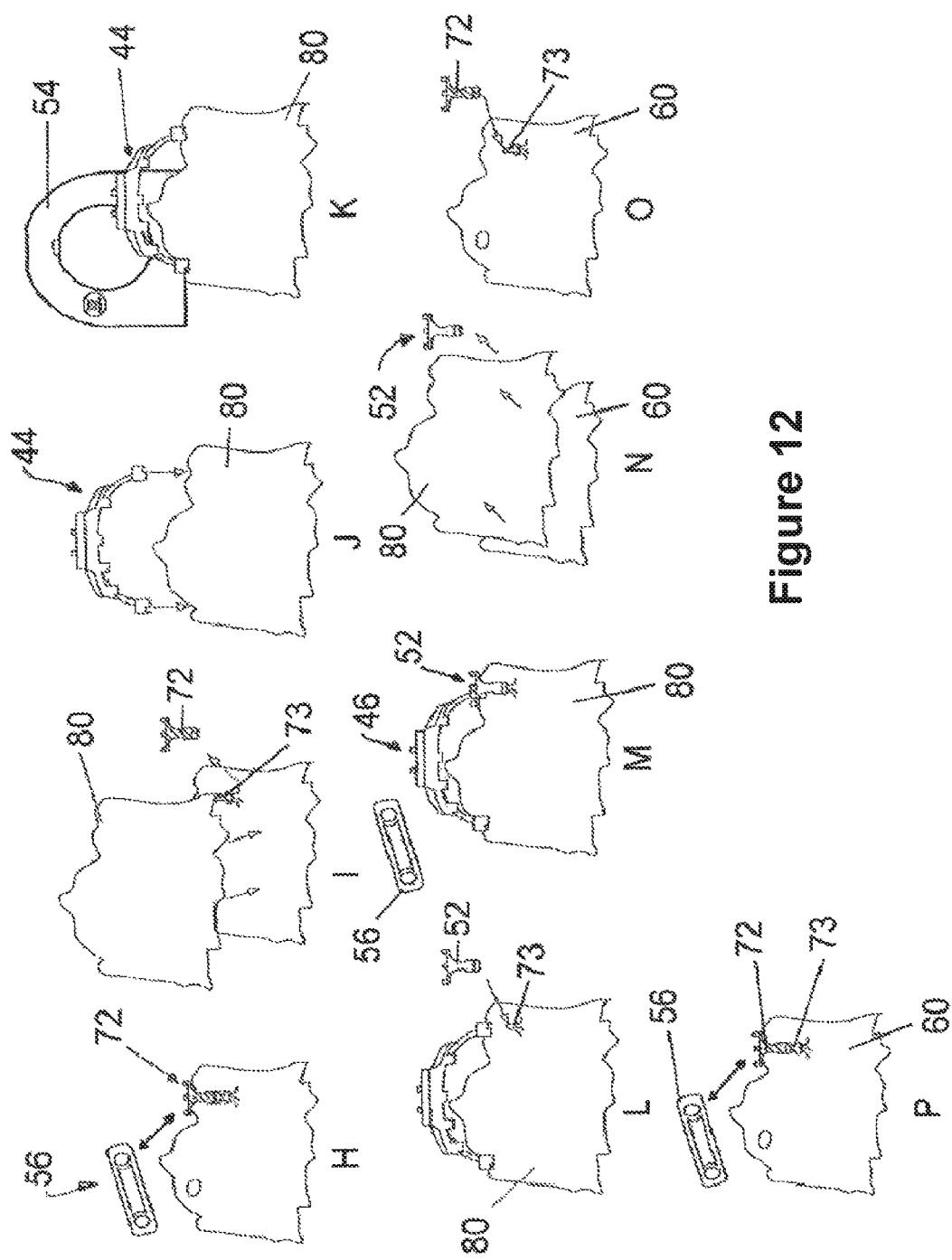

The steps of pre-operative imaging and registering are shown in A to D in FIG. 11. A patient's head 40 is immovably fixed in a skull clamp 42 which is used for navigationally assisted treatment to be performed on the head 40. The skull clamp 42 has a fixedly installed support 50 for a reference array 52, and a so-called MR matrix 44 comprising structures 48 to be imaged is to be mounted on the clamp 42. A tracking reference 46 is located on the MR matrix 44, in a known position with respect to the structures 48 to be imaged. Once the MR matrix 44 has been installed, the non-sterile reference array 52 is removed so that it does not become an obstruction during the scanning process. The patient is scanned together with the skull clamp 42 and the MR matrix 44 in step B, then the non-sterile reference array 52 is re-installed and a registering process is performed in step C using a camera system 56 of a medical tracking system. Because the positional relationship between the patient's anatomy and the reference array 46 is known via the scanned structures 48 which have a fixed position with respect to the array 46, and because the arrays 46 and 52 have a fixed and known positional relationship with respect to each other, the reference array 52 can then be used as a valid navigational reference with respect to the patient.

Once registration is complete, the non-sterile array 52 and the non-sterile clamping unit 53 are removed in step D, in order to prepare the patient for draping. After the drape 60 has been placed over the patient in step E, a sterile clamping unit 73 and a sterile reference array 72 are installed, above the drape 60, on the covered support (clamping block) 50 in step F. The connector is designed in accordance with the present invention; it comprises a support 50 and a clamping unit 73 and can thus be installed without a change in position as compared to the position of the non-sterile unit 53. The overall registration of the patient has not been influenced or altered by installing the sterile reference array 72 on the clamping unit 73, since the latter two have the same form as their non-sterile equivalents 52 and 53. Thus, navigation can immediately start in step G and continue in step H, as indicated in step H by the double-headed arrow between the tracking system 56 and the reference array 72.

If an intra-operative scan has to be made during the treatment, for example because of a positional shift in tissue, then the operating field must be kept sterile by covering it with another drape. To this end, the reference array 72 is removed and a second drape 80 is placed over the first drape 60, covering the sterile clamping unit 73, in step I.

With the sterile clamping unit 73 now sterilely covered, the non-sterile MR matrix 44 can then be re-mounted in step J, and the patient can be scanned again in step K. For the purpose of re-registering, the non-sterile array 52 is mounted on the covered clamping unit 73, which acts as a support for a clamping unit (not indicated by a reference numeral in FIG. 12) which is installed at the bottom of the reference array 52 in step L. In step M, a registration is performed which is valid for both the non-sterile reference array 52 and the sterile reference array 72, as explained above with reference to steps C to F.

In step N, the non-sterile reference array 52 is removed together with the second drape 80, thus uncovering the sterile drape 60 and the sterile clamping unit 73 on which the sterile reference array 72 can then be clamped.

Because, as explained above, the connector arrangement according to the present invention guarantees that no overall positional shift occurs with respect to the reference arrays, navigation can be resumed in step P using the new, intra-operatively acquired patient data.

It is to be noted that the validity of the registration could be re-verified prior to the navigation steps H and P, which would not have the scope of a complete re-registration and would not therefore obstruct the physician's workflow. Thus, connecting a reference array in accordance with the present invention and the workflow described above enables draping, registering, tracking and intra-operative scanning to be performed without puncturing the drape and thus impairing sterility and without obstructing the physician's workflow to any perceptible extent by necessitating additional registration processes.

The invention claimed is:

1. Apparatus for attaching an associated reference array in a fixed positional relationship with respect to an attachment area of an associated patient, wherein the associated patient is to be selectively covered by one or more associated sterile drapes in the attachment area, the apparatus comprising:
   a first connector comprising:
      a first support configured for selective attachment with the associated patient below a first associated drape of the one or more an associated sterile drapes, the first support defining a first connection surface; and a first clamping element comprising:
  a first set of at least two distinct clamps, the first set of at least two distinct clamps being selectively movable relative to the first connection surface defined by the first support thereby selectively catching the first associated drape of the one or more associated sterile drapes at one or more first clamping positions between the first support and the first set of at least two distinct clamps in such a way that a positional shift in the first clamping element relative to the first support as a result of clamping the first associated drape at the one or more first clamping positions is compensated for such that an overall positional shift in the first clamping element relative to the attachment area of the associated patient is substantially zero; and
  a second support operatively coupled with the first clamping element, the second support defining a second connection surface,
  wherein the first set of at least two distinct clamps are carried by the first clamping element at locations on the first clamping element distributed along positions relative to the first connection surface of the first support,
  wherein the first set of at least two distinct clamps are selectively movable towards the first connection surface of the first support to clamp the first clamping element with the first support; and
a second connector comprising:
  a second clamping element configured to directly or indirectly hold the associated reference array or an associated reference array adaptor relative to the second support and above an associated second drape, wherein the second clamping element comprises:
    a second set of at least two distinct clamps, the second set of at least two distinct clamps being selectively movable relative to the second connection surface defined by the second support thereby selectively catching a second associated drape of the one or more associated sterile drapes at one or more second clamping positions between the second support and the second set of at least two distinct clamps in such a way that a positional shift in the second clamping element relative to the second support as a result of clamping the second associated drape at the one or more second clamping positions is compensated for such that an overall positional shift in the second clamping element relative to the second support and to the attachment area of the associated patient is substantially zero,
  wherein the second set of at least two distinct clamps are carried by the second clamping element at locations on the second clamping element distributed along positions relative to the second connection surface of the second support,
  wherein the second set of at least two distinct clamps are selectively movable towards the second connection surface of the second support to clamp the second clamping element with the second support.

2. The apparatus according to claim 1, wherein:
the first set of at least two clamps comprise first distinct clamping contacts or first distinct clamping contact areas, the first distinct clamping contacts or first distinct clamping contact areas forming a first discontinuous clamping area; and
the second set of at least two clamps comprise second distinct clamping contacts or second distinct clamping contact areas, the second distinct clamping contacts or second distinct clamping contact areas forming a second discontinuous clamping area.

3. The apparatus according to claim 1, wherein:
the first set of at least two distinct clamps are arranged in one or more of:
  the first set of at least two distinct clamps clamp the first surface of the first support from directions which are orientated towards a symmetrical feature, comprising a plane or an axis of symmetry, of one or more of the first support and/or the first connection surface;
  the first set of at least two distinct clamps are arranged on different sides of the first support and clamp the first support from directly opposing directions or parallel directions;
  the first set of at least two distinct clamps comprise three or more clamps distributed substantially uniformly, along parallel flat surfaces of the first support and clamp the first support in one or more of parallel and/or anti-parallel and/or coincident and/or opposing directions;
  the first set of at least two distinct clamps comprise three or more clamps distributed substantially uniformly, along a curved surface or angled flat surfaces of the first support and clamp the first support from directions which intersect substantially at one point and in particular have an intersecting point which is arranged substantially on a plane or an axis of symmetry of the first support; and/or
  the first set of at least two distinct clamps are arranged such that their clamping direction lies at a right angle or parallel to the direction of a reference array holder which extends from the second clamping element; and
the second set of at least two distinct clamps are arranged in one or more of:
  the second set of at least two distinct clamps clamp the second surface of the second support from directions which are orientated towards a symmetrical feature, comprising a plane or an axis of symmetry, of one or more of the second support and/or the second connection surface;
  the second set of at least two distinct clamps are arranged on different sides of the second support and clamp the second support from directly opposing directions or parallel directions;
  the second set of at least two distinct clamps comprise three or more clamps distributed substantially uniformly, along parallel flat surfaces of the second support and clamp the second support in one or more of parallel and/or anti-parallel and/or coincident and/or opposing directions;
  the second set of at least two distinct clamps comprise three or more clamps distributed substantially uniformly, along a curved surface or angled flat surfaces of the second support and clamp the second support from directions which intersect substantially at one point and in particular have an intersecting point which is arranged substantially on a plane or an axis of symmetry of the second support; and/or
  the second set of at least two distinct clamps are arranged such that their clamping direction lies at a right angle or parallel to the direction of the reference array holder which extends from the second clamping element.

4. The apparatus according to claim 1, wherein:
the first clamping element and the first support cooperatively define a first set of clearances therebetween for freely accommodating the first associated drape of the one or more an associated sterile drapes, the first set of clearances being provided in-between contact points/areas of the first set of at least two distinct clamps; and
the second clamping element and the second support cooperatively define a second set of clearances therebetween for freely accommodating the second associated drape of the one or more an associated sterile drapes, the second set of clearances being provided in-between contact points/areas of the second set of at least two distinct clamps.

5. The apparatus according to claim 1, wherein:
the first clamping element comprises one or more of: a first bracket, a first flexible bracket, and/or a first forked bracket; and
the second clamping element comprises one or more of: a second bracket, a second flexible bracket, and/or a second forked bracket.

6. The apparatus according to claim 1, wherein:
the first clamping element comprises one or more first clamping arms which are or can be flexibly biased towards clamping positions, wherein the one or more first clamping arms are flexible at thinner arm portions spaced away from their respective clamping ends; and
the second clamping element comprises one or more second clamping arms which are or can be flexibly biased towards clamping positions, wherein the one or more second clamping arms are flexible at thinner arm portions spaced away from their respective clamping ends.

7. The apparatus according to claim 6, wherein:
the one or more first clamping arms or their respective clamping ends are or can be biased in the direction of the first support by at least one first biasing element anchored on a first rigid holder or slider configured to accommodate or encompass the first clamping element; and
the one or more second clamping arms or their respective clamping ends are or can be biased in the direction of the second support by at least one second biasing element anchored on a second rigid holder or slider configured to accommodate or encompass the second clamping element.

8. The apparatus according to claim 7, wherein:
the at least one first biasing element is anchored on the first rigid holder, and the first rigid holder is slidably mounted on the first clamping element; and
the at least one second biasing element is anchored on the second rigid holder, and the second rigid holder is slidably mounted on the second clamping element.

9. The apparatus according to claim 1, wherein:
the first set of at least two distinct clamps and the first support are selectively mutually slidably engagable at the one or more first clamping positions, such that a first clamping force direction is substantially constant and independent of any movements or bending by the first clamping element; and
the second set of at least two distinct clamps and the second support are selectively mutually slidably engagable at the one or more second clamping positions, such that a second clamping force direction is substantially constant and independent of any movements or bending by the second clamping element.

10. The apparatus according to claim 1, wherein:
the first set of at least two distinct clamps and the first support comprise corresponding first surface forms at the one or more first clamping positions, the first surface forms comprising one or more first extensions and first receptacles, convex and concave first parts or first hemispheres, and/or snugly fitting first surface forms; and
the second set of at least two distinct clamps and the second support comprise corresponding second surface forms at the one or more second clamping positions, the second surface forms comprising one or more second extensions and second receptacles, convex and concave second parts or first hemispheres, and/or snugly fitting second surface forms.

11. The apparatus according to claim 1, wherein:
the first clamping element comprises first clamping arms are selectively slidably moveable towards the one or more first clamping positions along a first linear guide, such that their sliding movement is a movement along a first linear axis; and
the second clamping element comprises second clamping arms are selectively slidably moveable towards the one or more second clamping positions along a second linear guide, such that their sliding movement is a movement along a second linear axis.

12. A method for attaching an associated reference array in a fixed positional relationship with respect to an associated patient, the method comprising:
covering both the associated patient and a first connector support with an associated first sterile drape, the first connector support being directly or indirectly attached with one or more of the associated patient and/or a patient holding device at an attachment area;
fastening a first clamping element above the associated first sterile drape, wherein the fastening the first clamping element comprises clamping the first connector support, with the drape caught between the two, by means of a first set of at least two distinct clamps, the first set of at least two distinct clamps being selectively movable relative to a first connection surface defined by the first connector support thereby selectively catching the associated first sterile drape at one or more clamping positions between the first connector support and the first set of at least two distinct clamps in such a way that a positional shift in the first clamping element relative to the first connector support as a result of clamping the associated first sterile drape at the clamping position is compensated for, such that an overall positional shift in the first clamping element relative to the attachment area of the associated patient is substantially zero;
covering the associated first sterile drape, the first clamping element, the first connector support, a second connector support, and the associated patient with an associated second sterile drape, the second connector support being operatively coupled with the first clamping element; and fastening a second clamping element above the associated second sterile drape, wherein the fastening the second clamping element comprises clamping the second connector support, with the drape caught between the two, by means of a second set of at least two distinct clamps, the second set of at least two distinct clamps being selectively movable relative to a second connection surface defined by the second connector support thereby selectively catching the associated second sterile drape at one or more clamping positions between the second connector support and the second set of at least two distinct clamps in such a way that a positional shift in the second clamping element relative to the second connector support as a result of clamping the associated second sterile drape at the clamping position is compensated for, such that an overall positional shift in the second clamping element relative to the second connection surface and relative to the attachment area of the associated patient is substantially zero.

* * * * *